United States Patent [19] [11] 4,006,153
Bochis [45] Feb. 1, 1977

[54] ANTHELMINTIC BENZIMIDAZOLES WITH IMPROVED AQUEOUS STABILITY
[75] Inventor: Richard J. Bochis, East Brunswick, N.J.
[73] Assignee: Merck & Co., Inc., Rahway, N.J.
[22] Filed: Oct. 25, 1974
[21] Appl. No.: 518,139
[52] U.S. Cl. .................................. 260/302 H; 424/270
[51] Int. Cl.$^2$ ....................................... C07D 417/04
[58] Field of Search .............................. 260/302 H
[56] References Cited
UNITED STATES PATENTS
3,839,347  10/1974  Fisher et al. .................... 260/302 H Primary Examiner—R. Gallagher
Attorney, Agent, or Firm—David L. Rose; J. Jerome Behan

[57] ABSTRACT

Amine salts of substituted benzimidazoles with a carboxymethyleneamino group at the 1-position have been discovered to possess a markedly enhanced stability in aqueous solutions when compared with other salts. The improved salts are di- and tri-loweralkylamine salts.

3 Claims, No Drawings

ANTHELMINTIC BENZIMIDAZOLES WITH IMPROVED AQUEOUS STABILITY

BACKGROUND OF THE INVENTION

It is well known in the prior art that certain benezimidazole derivatives have substantial anthelmintic activity in sheep, cattle, and other domestic and wild animals. However, generally those compounds have minimal or non-existant water solubility which renders the compounds non-suitable for injectable administration and other forms of administration which require aqueous solutions. Often where a compound does demonstrate significant aqueous solubility, the solution thus formed is found to be unstable for the period of time necessary to provide for a usuable injectable formulation. The instant invention provides for more novel salts of anthelmintically active compounds, which salts are soluble in an aqueous medium and which produce solutions markedly more stable than prior art solutions.

DESCRIPTION OF THE PRIOR ART

Compounds having the formula:

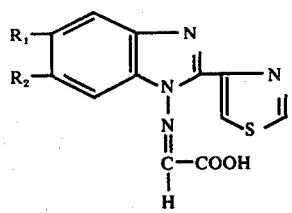

which are variously substituted at the 5- and 6-positions are disclosed in U.S. Pat. No. 3,839,347 as anthelmintic agents. Also disclosed are certain salts of the foregoing compounds which have improved aqueous solubility. It has been found, however, that markedly improved stability of the resultant aqueous solution can be obtained by the use of the novel salts of the instant invention with no loss in anthelmintic potency or degree of aqueous solubility.

SUMMARY OF THE INVENTION

The instant invention concerns the di- and tri- loweralkyl amine salts of compounds having the formula:

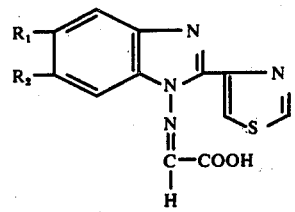

wherein $R_1$ and $R_2$ are hydrogen,

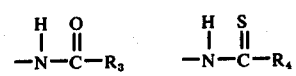

wherein $R_3$ is isopropoxy, phenyl or p-fluorophenyl; and $R_4$ is methoxy or pyrrolidinyl provided that only one of $R_1$ and $R_2$ is other than hydrogen in a single molecule.

It has been found that the di- and tri-loweralkyl amine salts exhibit a substantially improved stability in aqueous solution while maintaining significant solubility in said aqueous media and also maintaining a high level of anthelmintic activity.

The infection generically known as helminthiasis involves infestation of the body of warm-blooded animals and particularly the gastro-intestinal tract of man and domestic animals such as sheep, cattle, goats, swine, dogs, and poultry with certain species of parasitic worms known as helminths. Among the helmintic parasites, the most commonly occurring in domestic animals are those of the phylum nemathelminthes and particularly nematodes of the genera haemonchus, trichostrongylus, ostertagia, nematodirus, cooperia, bunostomum, oesophagostomum, chabertia, trichuris, ascaris, capillaria, heterakis, and ancylostoma. The diseases attributable to parasitic infections of these organisms, for example ascariasis, trichostrongylosis, and gross parasitism are wide spread in occurrence and serious in nature. The diseased host almost inevitably suffers from such conditions as malnutrition, anemia, and general weakness and malaise. In addition to the above conditions which necessitate increasing the nutrient intake of the host, helminthiasis may well have more disastrous consequences. The diseased host may suffer from a severe inflamation of the intestinal lining which will result in hemorrhaging. Indeed in more advanced and uncontrolled cases, helminthiasis will lead to prostration and death. It will be apparent, therefore, that helminthiasis is a disease of major concern whether viewed from the aspect of public health or from the aspect of the economic loss resulting from helmintic infestation of domestic animals. Thus, the provision of improved composition and methods for the treatment and elimination of helminthiasis and the parasitic worms responsible for the disease is most highly welcomed.

Indeed, valuable compounds for use in the treatment and prevention of helminthiasis have been discovered. These compounds have proven to be very useful for the treatment of helminthiasis when administered orally. However, said compounds have generally not had sufficient water solubility to provide for injectable compositions. Certain salts of compounds of structural formula I have also been prepared, which compounds also provide for a high degree of anthelmintic activity. However, the surprising benefit afforded by the instant invention is the high degree of stability of the aqueous solutions formed by dissolving in water the diloweralkyl amino or triloweralkyl amino salts of the compounds of structural formula I.

The di- and tri-loweralkylamino salts of this invention are soluble up to concentration of 80% w/v in water which is advantageous for the preparation of small-volume injectable formulations. The stability of aqueous solutions of the salts of the instant invention is evident by the fact that a 60% solution of a trialkyl amine salt of 1-carboxymethylene amino, 5-isopropoxy-carbonylamino, 2-(4-thiazolyl) benzimidazole is still clear after storage at 30° C. after 21 days. Solutions of prior art salts are seen to have comparable solubilities in water, however, such solutions generally form precipitates in less than 3 days.

The high solubility of the salts of the instant invention is important for the injectable administration of compositions containing such salts. When compositions are administered subcutaneously or intramuscularly and the ingredients are not fully dissolved, the anthelmintic is not fully absorbed by the body tissue but rather remains partially encapsulated at the site of the injection. This result is undesirable since relatively large amounts of drug are thereby wasted and cannot be advantageously used. The encapsulatiion also creates hard abnormal areas beneath the skin at the site of the injection which resembles welts. The use of highly soluble compounds such as those described herein above in the subcutaneous or intramuscular injection of anthelmintic compositions eliminates encapsulation and permits complete utilization of the injected drug.

The novel salts of the instant invention possess, in aqueous solution, an unexpectedly high degree of stability in combination with the above described and highly desirable solubility in said aqueous media. It has been discovered that precipitation out of aqueous solution of a degration product of prior art salts begins to occur at a time which will preclude the successful marketing of aqueous solutions of said salts which are intended for injectable administration. In other words, the "shelf life" of said aqueous solutions is too short a period of time to allow for successful marketing of aqueous injectable compositions. The active ingredient decomposes and precipitates an insoluble decomposition product generally before the injectable composition reaches the ultimate consumer, thus rendering said injectable composition usuable.

Accordingly the present invention provides novel compositions, as indicated above, which are stable and effective in treatment, prevention, and control of helminthiasis; which are at the same time safe, effective and reliable when used for these purposes; and are easily and conveniently administered eliminating substantially the problems described hereinabove. It will be apparent within the purview of this statement that the novel salts of the present invention are effective in preventing the development of infective eggs and/or larvae of worms thereby minimizing the possibility of contamination and subsequent reinfestation.

Thus a particular advantage of the present invention is the provision of novel salts which utilizes the significant anthelmintic activity of the benzimidazoles described hereinabove as structural formula I, while incorporating these latter agents in salts of unexpectedly significant stability in combination with a high degree of water solubility. A further advantage resides in the enhanced anthelmintic activity possessed by the compounds of this invention and their component benzimidazoles when employed in the aqueous media as described herein.

The basic compounds of structural formula I are generally prepared by the treatment of an appropriately substituted 1-amino benzimidazole with glyoxylic acid. The substituted 1-amino benzimidazole is prepared by treating an amino group at the 5- and/or 6-position with the appropriate carbonyl halide or thio carbonyl halide. The halide is added to the 5(6) amino compound with stirring generally over a period of time which may extend from 5 minutes to 1 hour. The amino compound is generally combined with a base the purpose of which is to combine with and neutralize the hydrogen halide liberated during the reaction. At least one molar equivalent of the base is employed. The reaction mixture during the addition is generally cooled below ambient temperatures in order to compensate for the exothermicity of the reaction. Temperatures of between 0° and 20° C. are generally employed. Following the addition the reaction is generally stirred for from 2 to 24 hours at from 20° to 50° C. in order to complete the reaction. The product is then isolated and purified using techniques well known to those skilled in this art.

The 5(6) substituted 1-amino compound is then treated with glyoxylic acid to form the 1 carboxymethylene amino compound. The starting material and the glyoxylic acid are generally combined in a solvent and heated at from 50° C. to the reflux temperature of the reaction mixture for from 15 minutes to 5 hours. The solvent may be any suitably organic solvent such as alcohols exemplified by ethanol and isopropanol; and mixtures of such solvents with hydrocarbons such as benzene, toluene, hexane and the like. After the heating period the reaction mixture is cooled and the product isolated by techniques known to those skilled in this art.

The salts of 1-carboxymethylene amino 5(6) substituted 2-(4-thiazolyl) benzimidazole are then prepared by dissolving the starting material in water or a suitable organic solvent such as loweralkanol or a mixture of such loweralkanol solvent with a hydrocarbon solvent which has dissolved therein at least a single molar equivalent of a diloweralkylamine or a triloweralkylamine. The solution is stirred for from 5 minutes to 1 hour whereupon the salt is isolated from the solution and purified by techniques known to those skilled in this art The novel salts of this invention are preferably administered to the animal infected with helminths in the form of a parenteral composition. Owing to the high degree of water solubility of the instant salts the preferred parenteral composition consists of the said salts dissolved in sterile water or sterile saline. The amount of the salt contained in the composition will depend on the particular animal being treated, the size and weight of said animal, the animals's general physical condition and the extent and severity of the helmintic infection. Generally, however, the injectable composition will contain from 10 to 80% w/v of the salt in the aqueous medium. Preferred compositions will contain from 25 to 60% w/v of the salt in the injectable composition.

Optionally the salts of the invention may be combined in an oil base injectable composition preferably of the vegetable oil variety such as peanut oil, cotton seed oil and the like. The salt will be present in the oil base formulation to an extent equivalent to the aqueous formulation described above.

Although the anthelmintic agents of this invention find their primary use in the treatment and/or prevention of helminthiasis in domesticated animals, such as sheep, cattle, horses, dogs, swine and goats, they are also effective in treatment of helminthiasis that occurs in other living animals. The optimum amount to be employed for best results will, of course, depend upon the particular benzimidazole employed, the species of animal to be treated and the type and severity of helminth infection. Generally good results are obtained with our novel compounds by the oral administration of from about 5 to 125 mg. per kg. of animal body weight, such total dose being given at one time or in divided doses over a relatively short period of time such as 1–2 days. With the preferred compounds of the invention, excellent control of helminthiasis is obtained in domesticated animals by adminstering from about 10 to 70 mg. per kg. of body weight in a single dose. The techniques for administering these materials to animals are known to those skilled in the veterinary field.

The best mode contemplated by applicants for carrying out their invention is set forth in the following examples; it being understood that these examples are for purposes of illustration merely and no limitation is intended except as set forth in the appended claims.

EXAMPLE 1

1-Carboxymethyleneamino-5-isopropoxycarbonylamino-2-(4'-thiazolyl) benzimidazole triethylamine salt To a solution of 410 ml. of anhydrous methanol containing 19 g. of triethylamine is added 65 g. of 1-carboxymethyleneamino-5-isopropoxycarbonylamino-2-(4'-thiazolyl) benzimidazole. The reaction mixture is stirred for 15 minutes until the mixture is homogeneous. The reaction mixture is filtered and diluted with diethylether in portions, until the solution is turbid. The solution is scratched or seeded with stirring whereupon additional ether is added to a total volume of 3300 ml. The suspension is stirred for 5 minutes to insure complete crystallization and filtered and washed with ether affording 81 g. of 1-carboxymethylene amino-5-isopropoxy-carbonyl-amino-2-(4'-thiazolyl) benzimidazole triethylamine salt. The salt is hygroscopic and is dried in vacuo at 65° C. affording a material with mp. of 126°–128°.

EXAMPLE 2

1-Carboxymethyleneamino-5-isopropoxycarbonylamino-2-(4'-thiazolyl) benzimidazole diethylamine salt To a solution of 25 ml. of methanol containing 246 mg. of diethylamine is added 1.23 g. of 1-carboxymethyleneamino-5-isopropoxycarbonylamine-2-(4'-thiazolyl) benzimidazole. The reaction mixture is stirred for 5 minutes whereupon a clear solution results. Diethylether is added (150 ml.) whereupon the salt precipitates. The suspension is stirred for 5 minutes and filtered. The solid material is washed with ether and dried affordiing 368 mg. of 1-carboxymethyleneamino-5-isopropoxycarbonylamino-2-(4'-thiazolyl) benzimidazole diethylamine salt.

EXAMPLE 3

1-Carboxymethyleneamino-5-isopropoxycarbonylamino-2-(4'-thiazolyl) benzimidazole triethylamine salt 1.84 g. of 1-carboxymethyleneamino-5-isopropoxycarbonylamino-2-(4'-thiazolyl) benzimidazole is suspended in 5 ml. of water and 5 ml. of water saturated with trimethylamine gas is added thereto. A solution is formed which is filtered and freeze-dried affording 2.029 g. of 1-carboxymethyleneamino-5-isopropoxycarbonyl-amino-2-(4'-thiazolyl) benzimidazole triethylamine salt.

EXAMPLE 4

1-Carboxymethyleneamino-5-isopropoxycarbonylamino-2-(4'-thiazolyl) benezimidazole dimethylamine salt Following the procedure of Example 3 employing 1.84 g. of 1-carboxymethyleneamino-5-isopropoxycarbonyl-amino-2-(4'-thiazolyl) benzimidazole, 0.434 g. of a 40% aqueous dimethylamine solution and 5.0 ml. of water, 1-carboxymethyleneamino-5-isoproproxycarbonylamino-2-(4'-thiazolyl) benzimidazole dimethylamine salt is prepared recovering 1.950 g.

What is claimed:
1. The triethylamine salt of 1-carboxymethyleneamino-5-isopropoxycarbonylamino-2-(4'-thiazolyl) benzimidazole.
2. The trimethylamine salt of 1-carboxymethyleneamino-5-isopropoxycarbonylamino-2-(4'-thiazolyl) benzimidazole.
3. The diethylamine salt of 1-carboxymethyleneamino-5-isopropoxycarbonylamino-2-(4'-thiazolyl) benezimidazole.

* * * * *